United States Patent [19]

Haindl

[11] Patent Number: 4,883,470
[45] Date of Patent: Nov. 28, 1989

[54] SAFETY CAP

[75] Inventor: Hans Haindl, Melsungen, Fed. Rep. of Germany

[73] Assignee: B. Braun Melsungen AG, Melsungen, Fed. Rep. of Germany

[21] Appl. No.: 245,578

[22] Filed: Sep. 20, 1988

[30] Foreign Application Priority Data

Sep. 25, 1987 [DE] Fed. Rep. of Germany ... 8712926[U]

[51] Int. Cl.$^4$ ............................................. A61M 5/32
[52] U.S. Cl. .................................. 604/192; 604/263
[58] Field of Search ...................... 604/192, 263, 187

[56] References Cited

U.S. PATENT DOCUMENTS 4,237,882 12/1980 Wickham .......................... 604/192
4,610,667 9/1986 Pedicano et al. ............... 604/263 X
4,740,205 4/1988 Seltzer et al. ....................... 604/192

Primary Examiner—John D. Yasko
Attorney, Agent, or Firm—Spensley Horn Jubas & Lubitz

[57] ABSTRACT

A safety cap having radial projections which comprise a slide flank inclined in the peripheral direction relative to the longitudinal axis of the sleeve of the safety cap. The slide flanks are engaged by the longitudinal wings of the cannula hub, which wings fit tightly to the inner wall surface between the radial projections.

Subject to the orientation of the peripherally inclined slide flank of each radial projection, the rotation of the safety cap loosely put together with the cannula hub causes a clamping lock in one direction or the other of the safety cap and the cannula hub by a mutual blocking of the radial projections and the longtiudinal wings, on the one hand, or an axial displacement of the safety cap from the cannula hub on the other hand. By a keying effect of the longitudinal wing of the cannula hub sliding over the oblique slide flank, the adhesion between the longitudinal wings and the inner wall surface is cancelled without a tractive effect endangering the connection of syringe cone and cannula hub, and the cannula is ready for use.

9 Claims, 2 Drawing Sheets

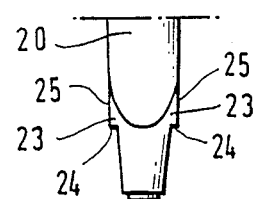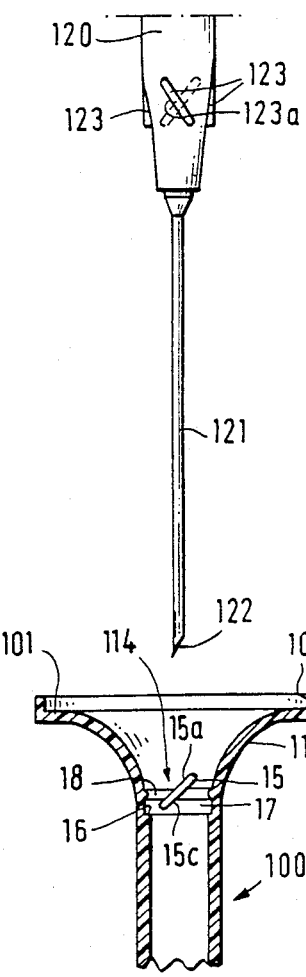
FIG.1
FIG.2

SAFETY CAP

BACKGROUND OF THE INVENTION

1. Field of the Invention

The invention relates to a safety cap for connecting a cannula hub to a cannula comprising a sleeve having a tubular wall whose one end contains an axial aperture from which extends an outwardly flared cone-shaped funnel and in whose range radial projections are designed on the inner wall surface which, in case of rotation of the sleeve, cooperate with longitudinal wings at the cannula hub.

2. Description of Related Art

One of the most frequent professional accidents is caused by being stuck by a used cannula with resultant infections. Therefore, the rules for accident prevention provide that, upon the use of the cannula, cannula safety caps which do not have a cone-shaped funnel should not be slipped on again, because the repeated slip-on of such safety caps is particularly risky. As recommended by the rules for prevention of accidents, the used cannula without the safety cap should be thrown directly into a specific cannula bin. Said recommendation is rather doubtful for several reasons: Cannula bins are not always available where injections are made or blood is removed by a physician, and the risk of an accident during the transport of the unprotected cannula to a cannula garbage bin is big; for removing the unprotected cannula from the syringe and for throwing it into a bin, the cannula hub must be often gripped with the resultant risk that the fingers come into contact with matter from the patient; the disposal of a non-protected cannula in an optional container, e.g. a bag, highly endangers the waste disposal staff.

A safety cap of the type mentioned at the outset hereof and disclosed in U.S. Pat. No. 4,610,667 is adapted to reduce the safety risk during the assembling with the used cannula in that, by the cone-shaped funnel, the sharp cannula tip is introduced into the opening of the sleeve so that, due to the reduced target accuracy of the user, stick wounds caused by a used cannula at his hand holding the safety cap are avoided. Further, in case of approximation of the used cannula, the cone-shaped funnel forms a protection against infected fluid dripping from said used cannula. To keep the cannula hub and the safety cap together during the waste disposal, there are provided flexible gripper arms directed radially inwardly which engage the cannula hub like barbs to prevent both elements from being moved apart axially. Said configuration calls for a specific measure to permit the separation of the safety cap from the unused cannula. To this effect, between cone-shaped funnel and cannula hub, there are formed flaps adapted to be broken away and keeping the cannula hub out of reach of the gripper arms. Said flaps need be broken down in order to allow the removal of the safety cap. In connection with a cannula hub assembled with a syringe cone, this is effected by a vigorous rotation of the safety cap. Such a procedure is most circumstantial. It is another disadvantage that, by unintentional exertion of axial force, the safety cap may be shifted against the cannula hub thus causing operativeness of the gripper arms so that the safety cap cannot be removed. After all, the cannula/safety cap assembly becomes useless and has to be replaced. Moreover, when the flaps are broken down, plastic particles may be set free which unfavorably may adhere to the cannula thus endangering the patient. Removal of the used cannula with the reapplied safety cap from the syringe cone is faciliated in that the longitudinal wings of the cannula hub extend between the projections formed between paraxial longitudinal flanges on the inner wall surface of the safety cap. If the latter is turned on the cannula hub, they abut against the longitudinal flanges so that the safety cap is arrested nonrotatingly on the cannula hub to serve as a means for the contactless, contamination-resistant removal of the cannula from the syringe cone.

It is the object of an invention to improve the safety cap mentioned at the outset hereof so that the axial removal of said safety cap from the unused cannula secured to a syringe is facilitated.

SUMMARY OF THE INVENTION

The posed problem is solved according to the invention in that the radial projections comprise at their outside facing the cone-shaped funnel, a slide flank being inclined in peripheral direction relative to the longitudinal axis of the sleeve and being engaged by the longitudinal wings of the cannula hub, which wings fit tightly to the inner wall surface between the radial projections.

Subject to the orientation of the peripherally inclined slide flank of each radial projection, the rotation of the safety cap loosely put together with the cannula hub causes a clamping lock in one direction or the other of safety cap and cannula hub by a mutual blocking of radial projections and the longitudinal wings, on the one hand, or an axial displacement of the safety cap from the cannula hub on the other hand. By a keying effect of the longitudinal wing of the cannula hub sliding over the oblique slide flank, the adhesion between the longitudinal wings and the inner wall surface is cancelled without a tractive effect endangering the connection of syringe cone and cannula hub, and the cannula is ready for use. The radial projections comply with a double duty facilitating, upon use, the common removal of protective cap and cannula hub from the syringe cone, and, prior to the use, the removal of the safety cap from the cannula hub. In both cases, due to the cone-shaped funnel, the user does not contact the cannula hub, so that he, himself, and the patient as well, are protected against contaminations and infections. The slide flank of each radial projection of the safety cap acting as an automatic kick mechanism for the safety cap in case of its rotation, the separating force is so small that the rentention force between the connecting members of the cannula hub and the syringe reliably ensures that both elements are kept together during the removal of the safety cap. When the safety cap is removed, the cannula hub may not be separated unintentionally from the syringe and germs may not be entrained either into the medicamental path by the repeated application of the cannula. The sterile drug administering means remains closed and contaminations may not penetrate into the drug.

The longitudinal wings of the cannula hub may extend in parallel to its longitudinal axis and may be provided with a transverse step confronted with the cannula and cooperating with the slide flank of the radial projection of the safety cap. Alternatively, each longitudinal wing of the cannula hub may ascend obliquely to the longitudinal axis. In such a case, longitudinal wings and slide flanks cooperate like an external and internal thread to ensure, in one sense of rotation of the safety cap, their clamping with the cannula hub against an axial divergent movement or, in the other sense of rotation, the axial separation of the two elements.

According to an advantageous embodiment, the slide flank extends at an angle of 15° to 45°, preferably of 20° to 30° with respect to the longitudinal axis of the sleeve. In case of oblique longitudinal wings, their pitch angle may correspond to the pitch angle of the slide flanks.

Each radial projection of the invention may be designed as an oblique rib having two parallel longitudinal edges of which the outer edge forms the inclined slide flank. The number of ribs corresponds to the number of longitudinal wings. At least two, preferably four pairs are provided which are uniformly distributed over the peripheries of safety cap and cannula hub.

In another embodiment of the invention, each radial projection is an axial profile having a stop edge parallel to the longitudinal axis of the sleeve, the external transverse edge of the axial profile forming the inclined slide flank. If so, an enlarged clamping surface is formed for the paraxial longitudinal wing of the cannula hub by the paraxial stop edge of the axial profile so that, in case of rotation, the static friction between safety cap and cannula hub is considerably increased, it being possible to reliably remove from the syringe the safety cap in common with the contaminated cannula to throw them away. The inner surface of the axial profile may slope wedgewise peripherally from the stop edge. As a result, in case of rotation of the safety cap relative to the cannula hub, a guided movement of the longitudinal wings on the slide flanks is realised. To further faciliate handling, the axial profiles are provided in a cylindrical extension of a larger diameter of the sleeve whose outer periphery comprises a bead.

The funnel opening of the cone-shaped funnel preferably of a circular cone funnel type having a smooth inner surface, preferably extends at an angle of about 45° relative to the longitudinal axis of the sleeve. The smooth inner surface forms an obstacle-free guide path for the striking cannula tip. As a result of the inclination of the cone-shaped funnel wall at an angle of about 45° relative to the longitudinal axis of the sleeve, the cone-shaped funnel is enlarged to at least double the diameter of the sleeve, i.e. the opening at the external edge of the cone-shaped funnel is nearly double as large as at the mouth of the sleeve. The axial length of the wall of the cone-shaped funnel should at least correspond to half the diameter of the maximum opening width. The prolongation of the cone-shaped funnel wall beyond said size is possibly limited by the fact that the package of the cannula with safety cap will become voluminous. With the mentioned preferred dimension, this problem may be eliminated in that cannula and safety cap are offset each layerwise by one funnel length to be stacked in the cardboard box so that the increase in volume remains negligeable.

Preferably, the wall of the cone-shaped funnel is straight. A vault convexly directed to the inside would cater for the need of an inward guiding of a cannula tip towards the sleeve cavity, and such a trumpet cup would improve the protective effect of the cone-shaped funnel against an insertion of the cannula tip past the sleeve opening.

It is possible to obtain another improvement in that, at the external edge of the cone-shaped funnel, a flange is provided which radially points outwardly. In any case, a hand holding the safety cap would not be shielded only against stick wounds and infected fluid dripping from the used cannula, but in case of the simplified removal of the safety cap from the cannula, according to the instant invention, the cone-shaped funnel protects said cannula against manual contact.

BRIEF DESCRIPTION OF THE DRAWINGS

Embodiments of the invention are illustrated in the drawing in which

FIG. 1 shows a cannula and a partial longitudinal section of a view of a safety cap including the radial projections with oblique slide flank, FIG. 2 is a modified cannula and the longitudinal section of a changed cone-shaped funnel range of another safety cap.

DESCRIPTION OF THE PREFERRED EMBODIMENT

Figure 3:
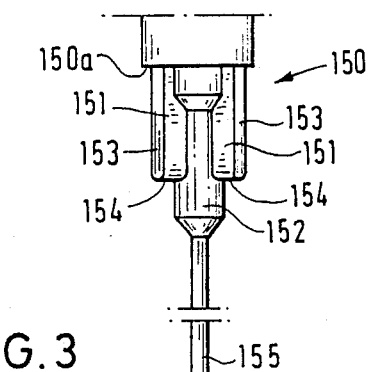
FIG. 3 is a cannula and a longitudinal section of a safety cap showing a second embodiment of the radial projections with oblique slide flank and FIG. 4 shows a cross section of the safety cap according to FIG. 3 along line IV—IV.

As shown in FIG. 1, a safety cap 10 for an injection cannula 21 having a sharply ground tip 22 and being secured to a hollow cannula hub 20 with inner cone consist of a substantially cylindrical (or profiled) sleeve 11 whose tubular wall 12 is closed all around and whose bottom portion 13 may be closed or open to allow the sterilization of the interior sleeve space. The total safety cap 10 is a plastic injection molding having a circular cross section. The end opposite to the bottom portion 13 of the straight sleeve 11 is provided with an axial opening 14 in whose direct vicinity, on the inner face of the wall 12, at least two opposite radial ribs 15 are provided which each comprise an external slide face 15a inclined in peripheral direction in the same sense at an angle of about 45° relative to the longitudinal axis of the safety cap 10 and an internal longitudinal edge 15c extending in parallel thereto. Seen in plan view on the surface of rib 15 facing the sleeve center—the direction of each rib 15 is oriented inwardly to the left from the opening 14 (outer end 15b). The radial height of the straight ribs 15 is equal and, they extend lengthwise from the mouth of opening 14 to the inner border 16 of an annular recess 17. The upper edge of said annular recess 17 is adjacent to an annular bead 18 radially directed inwardly and extending peripherally between the ribs 15. From the cross sectional viewpoint, said annular bead 18 has a round head, and it serves as a counterclamping member for the straight paraxial edge 25 of at least two paraxial longitudinal wings 23 disposed oppositely on the periphery of the cannula hub 20 for the clamping assembly of safety cap 10 and cannula hub 20 prior to and after the use of the cannula 21. A transverse step 24 of each longitudinal wing 23 abuts against the inner border 16 of the annular recess 17 thus forming a stop for the insertion depth to avoid a damage of the cannula tip 22 by the bottom 13 of the safety cap 10.

To remove the safety cap 10 from the cannula 21 to be used and remaining connected to the cone of a syringe, the safety cap 10 is slightly turned to the right (seen from the closed end), whereby step 24 of each longitudinal wing 23 slides over the oblique external slide flank 15a of the coordinated rib 15 and the safety cap 10 is pressed away wedgewise from the cannula hub 20. For separating the used cannula 21 from the syringe cone, the safety cap 10 is clampingly applied again onto the cannula hub 20 and turned to the left (seen from the closed end). At the same time, the lateral faces of the longitudinal wings 23 are applied against the outer end 15b of ribs 15 to thus cause a nonrotating connection of cannula hub 20 and safety cap 10 so that the latter is arrested on the cannula hub 20. During the left-hand rotation, the torque is fully transmitted, and the cannula hub 20 is easily detachable from the syringe cone, while the cannula 21 remains in the safety cap 20. Thus, the cannula hub 20 which is possibly contaminated need not be contacted by the fingers of the user for the separation of syringe and cannula 21. If syringe and cannula hub 20 are not put together via cone connections, but if they are screwed together by right-hand thread portions, the oblique position of the ribs 15 should be opposite to the illustration in FIG. 1 so that, during the rotation of the safety cap 10 for its removal from the cannula hub 20, the connection of the latter with the syringe cone is maintained.

Wall 12 of sleeve 11 of safety cap 10 is flared outwardly at opening 14 to merge with a circular cone-shaped funnel 19 opening at an angle of about 45° to at least double the diameter of sleeve 11. Preferably, the opening 30 of the cone-shaped funnel 19 has a maximum diameter of 17 mm and the axial length of the wall of the cone-shaped funnel 19 is about 6 mm. The wall inside of the cone-shaped funnel 19 is smooth to ensure that with the abutment of the tip 22 of the cannula 21 against the funnel surface, said tip 22 may be freely guided into the opening 14. The used cannula 21 inserted in the safety cap 10 may be removed therewith from a syringe so that cannula hub 20 is not contacted and a danger of infection is excluded for the user accordingly. At the same time, the cone-shaped funnel 19 has a protective effect for the user.

According to the embodiment of FIG. 2, the opening 114 of the safety cap 100 is provided with another cone-shaped funnel design 119. In this case, the wall of the cone-shaped funnel 119 is curved convexly to the inside thus forming a cup on whose inner surface the tip 122 of a cannula 121 may slide into the aperture 114 of the safety cap 100. The protective effect of the cup funnel 119 shaped circularly in plan view, is additionally increased in that the border 101 is prolonged as an outwardly directed radial flange and that the external edge of the border 101 is an upwardly projecting border 102 which forms another antislip protection for the cannula tip 122. The outfit of the inside of opening 114 of the protective cap 100 corresponds to that of the opening 14 of FIG. 1. A modified cannula hub 120 of cannula 121 cooperates with said locking and release arrangement of the safety cap. In place of the paraxial longitudinal wings 23 of the cannula hub 20, there are provided longitudinal wings 123 inclined relative to the longitudinal axis and oriented in the same direction as the ribs 15. The angular position of the longitudinal wings 123 corresponds to that of the ribs 15 as well. Upon rotation to the right (seen from the closed end) of the safety cap 100 clampingly put together with the cannula hub 120 by means of the annular bead 18, the lower inclined edge 123a of each oblique longitudinal wing 123 slides over the upwardly pointing slide flank 15A of each rib 15, and the safety cap 100 is axially pressed away by the cannula hub 120. In case of an opposite rotation of the safety cap 100, the oblique surfaces 15a and 123a are compressed correspondingly, the torque is fully transmitted, the cannula hub 120 left in connection with the safety cap 100 easily gets free from the syringe cone and may be disposed without any risk.

Figure 4:
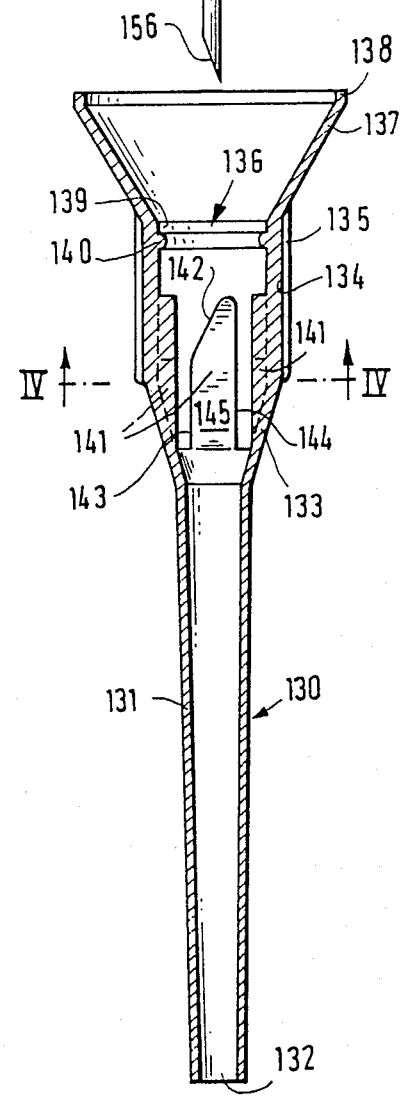
Figure 4:
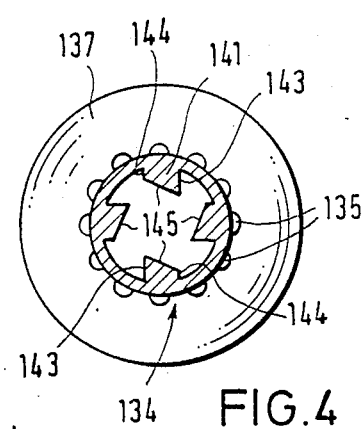

The principle of the embodiment of FIGS. 3 and 4 corresponds to that of FIGS. 1 and 2. A safety cap 130 of rigid plastic material consists of a tubular sleeve 131 whose lower end 132 is open for sterilizing the interior sleeve space and whose other end merges via a conical enlargement 133 into a cylinderical extension 134 whose inner diameter is larger than that of sleeve 131. The outer surface of extension 134 is provided with a bead 135 facilitating the handling of the safety cap 130. A circular opening 136 of the extension 134 is joined by an outwardly flared cone-shaped funnel 137 of a circular cross section. The upper edge 138 of the cone-shaped funnel 137 extends cylindrically upwardly. At the transition between cone-shaped funnel 137 and extension 134, there is a cylindrical step 139 which, on its inside, is limited by a radial annular bead 140. Beneath said annular bead 140 and somewhat spaced therefrom, but still within the range of opening 136, there are four axial profiles 141 in the form of straight ridges which, on the internal face of extension 134, are radially directed inwardly and which, at their end confronted with the cone-shaped funnel 137, include an inclined slide flank 142 while their other end flatly extends freely at the transition of the cone-shaped enlargement 133. Due to the oblique slide flank 142, each axial profile 141 is provided with a stop edge 143 and, parallel thereto, with a longer longitudinal edge 144.

On the inwardly directed inner face 145, each axial profile 141 is chamfered wedgewise in peripheral direction, such as obvious from FIG. 4. The chamfer evenly descends from the shorter stop edge 143 towards the longitudinal edge 144. The slide flank 142 of each axial profile 141 is inclined at an angle of 30° relative to the longitudinal axis of the safety cap 130—seen in plan view on the surface 145 facing the sleeve center oriented inwardly to the left from the opening 136.

A cannula hub 150 fitting with the safety cap 130 is provided with a usual, non-illustrated inner cone for a connection to the outer cone of a syringe. It comprises four longitudinal wings 151 distributed at equal distances over its periphery. Each longitudinal wing 151 being radially directed outwardly from a central boss 152 is provided with a straight, paraxial border 153 and with a step 154 directed transversely to the longitudinal axis of the cannula hub 150. A steel cannula 155 with a ground tip 156 is paraxially embedded into boss 152.

If the cannula hub 150 is put together with the safety cap 130, its edge 150a abuts against the outer surface of the annular bead 140 of the safety cap 130 thus ensuring that the tip 156 of the cannula 155 does not project downwardly beyond the open end 132 of the safety cap 130. The borders 153 firmly rest against the inner face of the extension 134 between the axial profiles 142 so that, by static friction, not only prior to but also upon the use of the cannula 155, a coherence is ensured between cannula hub 150 and safety cap 130. To allow to freely remove the safety cap 130 from the cannula hub 150 assembled with a syringe cone, the safety cap 130 (seen from the closed end) is turned to the right so that the steps 154 of the longitudinal wings 151 slide over the raised slide flanks 142 of the axial profiles 141 while the safety cap 130 is axially shifted away wedgewise from the cannula hub 150. For a contactless separation of the used cannula 155 from the syringe cone, the safety cap 130 is redisposed on the cannula hub 150 and—seen from the closed end—by a rotation to the left of the safety cap 130, the border 153 of each longitudinal wing 151 slides from the lower longitudinal edge 144 on the wedge-shaped inner face 145 of each axial profile 141 and is firmly pressed against this face 145 which, by an increased static friction between the elements and a nonrotatability with respect to each other, ensure a mutual locking of cannula hub 150 and safety cap 130 so that both parts may be easily removed in common from the syringe cone.

What is claimed is:

1. A safety cap for connection with a cannula hub of a cannula, the cannula hub having a plurality of longitudinal wings, the safety cap comprising:

a substantially longitudinal sleeve having a tubular wall and an axial aperture, an outwardly flared funnel extending from the axial aperture of the sleeve, a plurality of radial projections on the inner surface of the longitudinal sleeve, at least one of the radial projections comprising a slide flank inclined relative to the longitudinal axis of the sleeve and positioned to engage at least one of the longitudinal wings of the cannula hub during relative rotation of the cannula hub and the sleeve, the radial projections being positioned so that the longitudinal wings of the cannula hub fit tightly to the inner wall surface of the sleeve between the radial projections when the safety cap and the cannula hub are in connection.

2. A safety cap as set forth in claim 1, wherein the slide flank is provided at an angle of between 15° and 45° relative to the longitudinal axis of the sleeve.

3. A safety cap as set forth in claim 1, wherein the slide flank is provided at an angle of between 20° and 30° relative to the longitudinal axis of the sleeve.

4. A safety cap as set forth in claim 1, wherein each of the radial projections further comprises:

an oblique rib having an inner longitudinal border and an outer longitudinal border, the inner longitudinal border and the outer longitudinal border being substantially parallel, the outer longitudinal border of the oblique rib forming the slide flank of the radial projection.

5. A safety cap as set forth in claim 1, wherein each of the radial projections further comprises:

an axial profile having a stop edge substantially parallel to the longitudinal axis of the sleeve and an external transverse border, the external transverse border of the axial profile forming the slide flank of the radial projection.

6. A safety cap as set forth in claim 5, wherein the axial profile further comprises an inner face extending in a peripheral direction from the stop edge to thereby form a wedge.

7. A safety cap as set forth in claim 5, further comprising:

a cylindrical extension having a diameter larger than the diameter of the sleeve and having a peripheral bead, the axial profiles being disposed in the cylindrical extension.

8. A safety cap as set forth in claim 1, wherein the cannula hub has a substantially longitudinal axis and the longitudinal wings of the cannula hub are parallel to the longitudinal axis of the cannula hub, and wherein each of the longitudinal wings are further provided with a transverse step facing the cannula.

9. A safety cap as set forth in claim 1, wherein the cannula hub has a substantially longitudinal axis and wherein each of the longitudinal wings of the cannula hub ascends obliquely to the longitudinal axis of the cannula hub.

* * * * *